United States Patent
Richard et al.

(10) Patent No.: US 9,073,035 B2
(45) Date of Patent: Jul. 7, 2015

(54) CATALYST AND CATALYST CARRIER

(71) Applicant: Saint-Gobain Ceramics & Plastics, Inc., Worcester, MA (US)

(72) Inventors: Michael A. Richard, Fulshear, TX (US); John R. Lockemeyer, Sugar Land, TX (US)

(73) Assignee: Saint-Gobain Ceramics & Plastics, Inc., Worcester, MA (US)

( * ) Notice: Subject to any disclaimer, the term of this patent is extended or adjusted under 35 U.S.C. 154(b) by 159 days.

(21) Appl. No.: 13/648,303

(22) Filed: Oct. 10, 2012

(65) Prior Publication Data

US 2014/0100379 A1    Apr. 10, 2014

Related U.S. Application Data

(60) Provisional application No. 61/547,089, filed on Oct. 14, 2011.

(51) Int. Cl.

| | |
|---|---|
| *B01J 21/04* | (2006.01) |
| *B01J 21/00* | (2006.01) |
| *B01J 27/198* | (2006.01) |
| *B01J 27/02* | (2006.01) |
| *C07D 301/04* | (2006.01) |
| *C07D 301/10* | (2006.01) |
| *B01J 23/50* | (2006.01) |
| *B01J 27/055* | (2006.01) |
| *B01J 35/10* | (2006.01) |
| *C07D 301/03* | (2006.01) |
| *B01J 8/02* | (2006.01) |

(52) U.S. Cl.
CPC ............... *B01J 27/02* (2013.01); *C07D 301/04* (2013.01); *C07D 301/10* (2013.01); *B01J 21/04* (2013.01); *B01J 23/50* (2013.01); *B01J 27/055* (2013.01); *B01J 35/1085* (2013.01); *B01J 35/109* (2013.01); *B01J 35/1095* (2013.01)

(58) Field of Classification Search
CPC .... C07D 301/10; C07D 301/04; C07C 29/00; B01J 29/00; B01J 21/04; B01J 27/02; B01J 35/109; B01J 35/1095; B01J 35/1085; B01J 23/50; B01J 27/055
USPC ............ 549/523; 502/219, 243, 439; 422/211
See application file for complete search history.

(56) References Cited

U.S. PATENT DOCUMENTS

| | | | | |
|---|---|---|---|---|
| 5,100,859 | A * | 3/1992 | Gerdes et al. | 502/439 |
| 6,313,325 | B1 * | 11/2001 | Shima et al. | 549/534 |
| 6,831,037 | B2 * | 12/2004 | Szymanski et al. | 502/355 |
| 2009/0177016 | A1 | 7/2009 | Lockemeyer et al. | |

* cited by examiner

*Primary Examiner* — T. Victor Oh
(74) *Attorney, Agent, or Firm* — Stewart A. Fraser

(57) ABSTRACT

The carrier of the present invention includes at least 85 wt percent alpha alumina, at least 0.06 wt percent $SiO_2$ and no more than 0.04 wt percent $Na_2O$. The carrier has a water absorption no greater than 0.35 g/g and a ratio of water absorption (g/g) to surface area ($m^2$/g) no greater than 0.50 g/$m^2$. Another aspect of the invention is a catalyst for the epoxidation of olefins which comprises the above described carrier and silver dispersed thereon, where the carrier has a monomodal, bimodal or multimodal pore distribution and where the quantity of silver is between 5 and 50 wt %, relative to the weight of the catalyst. A reactor system for the epoxidation of olefins is also disclosed.

18 Claims, 2 Drawing Sheets

CATALYST AND CATALYST CARRIER

CROSS-REFERENCE TO RELATED APPLICATION

This application claims the benefit of U.S. Provisional Application No. 61/547,089 filed Oct. 14, 2011.

FIELD OF THE INVENTION

This invention generally relates to a carrier and a catalyst made from the carrier. More particularly, this invention is concerned with an alumina based carrier and a catalyst useful in the production of an olefin oxide, a 1,2-diol, a 1,2-diol ether, 1,2-carbonate, or an alkanolamine.

BACKGROUND OF THE INVENTION

In olefin epoxidation, feedstocks containing an olefin and an oxygen source are contacted with a catalyst disposed within a reactor under epoxidation conditions which results in the production of olefin oxide and typically includes unreacted feedstock and combustion products. The catalyst usually comprises a catalytically active material, such as silver, deposited on a plurality of ceramic pellets which may be referred to as carrier. Processes for making carrier are described in U.S. Pat. No. 6,831,037 and U.S. Pat. No. 7,825,062.

The technology used to manufacture carriers that are desirable for use as catalyst supports in an olefin epoxidation reaction has evolved substantially over the last few decades. In U.S. Pat. No. 4,007,135 (Hayden), which issued on Feb. 8, 1977, the description of example 4 discloses a carrier sold by Norton Co. wherein the "porosity to water was 25%" and the surface area of the carrier was 0.36 $m^2/g$. The description of example 7 in Hayden discloses a support which had a water porosity of 16 to 20% and a surface area of 0.17 $m^2/g$. In contrast to the descriptions in examples 4 and 7 in the Hayden reference, which may be generally described as disclosing carriers having low surface area and low pore volume, U.S. Pat. No. 5,187,140 (Thorsteinson), which issued on Feb. 16, 1993, discloses "a high surface area, high porosity carrier" (see column 6, lines 32-33) for the epoxidation of alkene to alkylene oxide. In column 7, lines 40-51, Thorsteinson describes the carriers of the subject invention as having a surface area greater than about 0.7 $m^2/g$ and, preferably, having a water pore volume of at least about 0.55 cc/g and most preferably from about 0.6 to about 0.8 cc/g. The '140 reference also discusses the teachings of the EP 0,327,356 (Jin); and U.S. Pat. No. 4,829,043 (Boehning) in the Background of the Invention section of the specification. The Jin reference is described as disclosing a carrier having "a total pore volume greater than 0.5 milliliters per gram, preferable 0.5 to 0.7 milliliters per gram" and "a surface area of 0.2 to 2 $m^2/g$, preferably 0.8 to 1.3 $m^2/g$". The Boehning reference is described as disclosing a carrier that "has a surface area of 0.4 to 0.8 $m^2/g$ and a pore volume of not less than 0.45 milliliter per gram." While the information in these references generally indicates that the technology used to manufacture carriers for catalysts used in the production of alkylene oxides has evolved from dense (i.e. low pore volume) and low surface area carriers to porous (i.e. high pore volume) and high surface area carriers there have been a few disclosures of low pore volume, high surface area carriers. For example, the '140 reference identified above also discloses CARRIER "AC" which was described as "available from the Norton Company, Stow, Ohio as 5502" and had a surface area of 0.80 $m^2/g$ and water pore volume of 0.26-0.32 cc/g. In another reference, Example 1A in US 2009/0192324 discloses an alpha alumina carrier having the following characteristics "(specific surface area: 1.0 $m^2/g$; water absorption: 35.7% by weight; $SiO_2$ content: 3.0% by weight; $Na_2O$ content: 0.35% by weight;". The general trend in the technical evolution of carriers described above, which has continued for approximately two decades, is believed to have occurred because the disclosed carriers did not provide the desired performance when used as a catalyst support.

A key driver behind the technical efforts to provide an improved catalyst has been to reduce the manufacturing cost of a reactor's final product (i.e. an olefin oxide) such as ethylene oxide. The cost of manufacturing can be impacted, both positively and negatively, in several ways which may be interrelated and thus complicated to isolate and improve upon. For example, the cost of the final product can be reduced if the selectivity of the reaction can be increased without a corresponding increase in the reactor's operating temperature. As used herein, selectivity is an indication of the proportion, usually represented by a percentage, of the converted material or product which is alkene oxide. If the carrier and catalyst can be changed so that the selectivity of the reactor is improved, then a higher percentage of the reactants are converted to the desired final product relative to the percentage of reactants converted with a previously used catalyst. The cost of the final product may also be reduced if the reactor's operating temperature can be reduced relative to another carrier that has generally equivalent or lower selectivity. Another tactic to reduce the cost of the final product is to improve the longevity of the catalyst which means that the reactor can be operated for longer periods of time before the selectivity and/or activity of the catalyst declines and/or the temperature increases to an unacceptable level which requires the reactor to be stopped so that the catalyst can be replaced. Stopping the reactor to replace the catalyst inherently incurs expenses that add to the cost of the final product.

With regard to the evolution of carrier and catalyst technology, the inventors of this application have recognized that there is a strong symbiotic relationship between changes made to the carrier and subsequent changes made to the catalyst which collectively improve or degrade the economic performance of the reactor. For example, as described above, some commercially available carriers have had low pore volumes, such as less than 0.35 g/g of catalyst, which may have limited the amount of catalytically active material (i.e. silver) which could be deposited. Limiting the amount of silver per gram of catalyst inherently limited the amount of silver per unit of volume within the reactor. However, carriers with total pore volume below 0.35 g/g, which may also be described as high density carriers, were resistant to crushing and abrasion which were desirable characteristics. Furthermore, the chemical composition of the carrier was substantially influenced by the impurities in the commercially available raw materials used to make the carrier. Some of the raw materials were the alumina, bond material and pore formers. Each of the raw materials had the potential to intentionally (or unintentionally) import excessive levels of certain compounds, such as $Na_2O$, $SiO_2$ and potassium containing compounds which could adversely impact the performance of the catalyst. To improve the performance of the catalyst researchers began to develop carriers that were more porous than their predecessors thereby increasing the amount of silver which could be deposited. Evidence of the move to developing more porous carriers can be found in the teachings in U.S. Pat. No. 7,547,795 (Matusz) which describes carriers of similar surface area, but with varying water absorption values. Furthermore, this patent teaches that increasing the water absorption of the carrier "allows for the loading of a greater amount of silver onto the support material than can be loaded onto other inorganic materials that have a lower water absorption." As the amount of silver per gram of carrier is increased, the amount of silver per unit of volume within the reactor is also increased which leads to improved selectivity and longevity. Unfortunately, increasing the porosity of the carrier reduces the carrier's resistance to crushing and increases its abrasion which are both undesirable attributes.

The goal of producing a carrier and catalyst that is both resistant to crushing and abrasion and enables selectivities and longevities beyond those commercially available has heretofore been difficult to achieve because of the perceived conflict between making a carrier with good resistance to crushing and abrasion while also providing useful porosity to allow for enough silver to be deposited onto a carrier and subsequently loaded into a reactor. The inventors of the invention described and claimed below have recognized that a carrier having certain micro physical and chemical characteristics, as will be explained, can improve the selectivity of the catalyst while providing a physically robust carrier thereby reducing the cost of the desired final product.

SUMMARY

Embodiments of the present invention provide a physically robust carrier that can withstand the crushing and abrasion forces typically experienced by a carrier during the carrier and catalyst manufacturing processes while also providing usable porosity and surface area and without the need to incorporate therein raw materials that include impurities which negatively impact the performance of a catalyst made from the carrier.

In one embodiment, the carrier of the present invention includes at least 85 wt percent alpha alumina, at least 0.06 wt percent $SiO_2$ and no more than 0.04 wt percent $Na_2O$. The carrier has a water absorption no greater than 0.35 gram of water/gram of carrier and a ratio of water absorption (gram of water/gram of carrier) to surface area ($m^2$ of carrier/gram of carrier) no greater than 0.50 gram of water/$m^2$ of carrier.

In another embodiment, this invention is a catalyst for the epoxidation of olefins. The catalyst comprises the above described carrier and silver dispersed thereon, where the carrier has a monomodal, bimodal or multimodal pore distribution and where the quantity of silver is between 5 and 50 wt %, relative to the weight of the catalyst.

In still another embodiment, this invention is a reactor system for the epoxidation of ethylene, which reactor system comprises at least one elongated tube having an internal tube diameter of between 20 and 50 mm, wherein contained is a catalyst bed of catalyst particles comprising silver in a quantity between 5 and 50 wt %, relative to the weight of the catalyst.

BRIEF DESCRIPTION OF THE DRAWINGS

FIG. 1 B is a graph of incremental pore volume curves;
FIG. 2 B is a graph of total incremental volume curves.

DETAILED DESCRIPTION

Figure 1A:
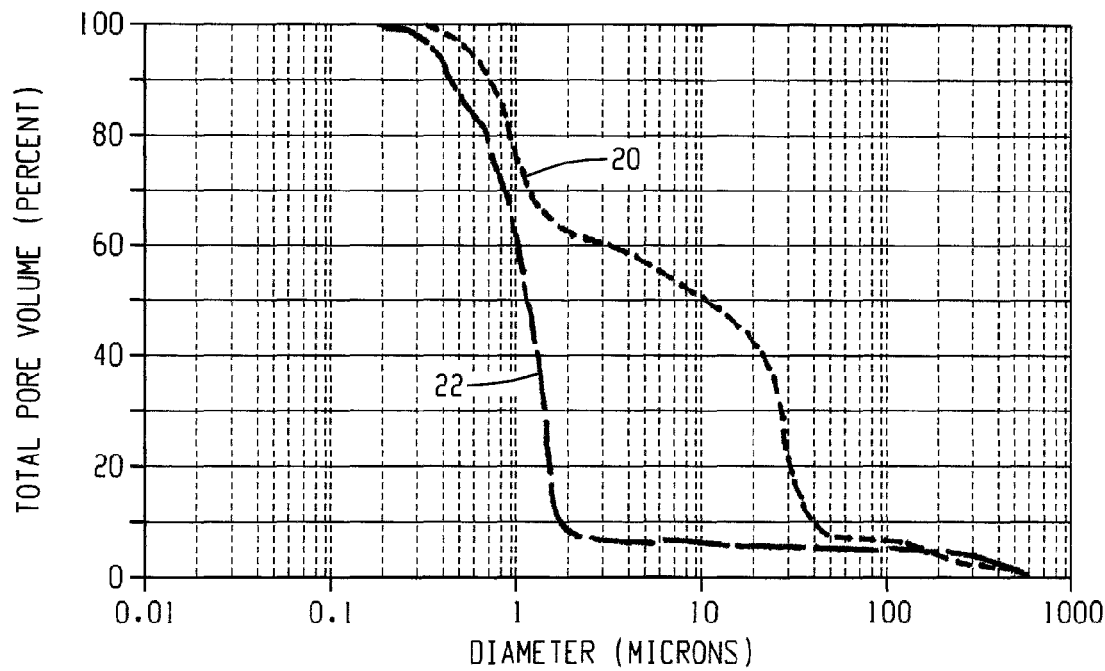
FIG. 1 A is a graph of total pore volume curves.

Porous ceramic bodies used as carriers for catalytically active material have numerous physical and chemical characteristics that collectively and individually influence the selectivity, longevity, yield and durability of the catalyst when disposed in a chemical reactor. The porous body's physical and chemical characteristics may also impact the manufacturability of the carrier and the catalyst. Numerous patents and technical articles have focused on improving the catalyst by modifying characteristics such as the carrier's surface area, water absorption, pore size distribution and morphology, which may be referred to herein as the carrier's micro physical characteristics. In other publications, the carrier's macro physical characteristics, such as its crush strength, resistance to abrasion, length, outer diameter and inner diameter, have been described. In yet other publications, the carrier's chemical characteristics, such as the amounts of potassium and silica, have been described. This invention describes a carrier and catalyst made therefrom which have a unique blend of micro physical characteristics and chemical characteristics that result in a catalyst which is both physically robust and provides the desired selectivity when used in a chemical reactor.

A carrier suitable for use as a substrate for catalytically active material has a functional lifetime, as defined herein, which begins when the carrier is formed as a discrete non-sintered pellet, known as greenware, and ends when the catalyst, which is formed from the carrier, is removed from a reactor. Many ceramic carriers, including carriers used to make catalyst for epoxidation processes, are exposed to various manufacturing processes and environmental conditions during their lifetime which could negatively impact the performance of the catalyst in a chemical reactor. The processes and environmental conditions described below could impact the performance of the catalyst by altering the physical and/or chemical characteristics of the catalyst in an undesirable manner.

From a physical point of view, two of the carrier's fundamental macro physical characteristics are its crush resistance and resistance to abrasion. To be commercially viable carriers should be sufficiently robust to withstand crushing and abrasion which may occur during one of several processing steps. For example, during the carrier manufacturing process, the carrier may be formed via an extrusion process that produces the greenware which may be small tubularly shaped pellets that are easily deformed by squeezing the greenware between a person's fingers. In commercial processes, the greenware may be loaded into large kiln cars which hold thousands of greenware pellets piled randomly on top of one another. The greenware at the bottom of the car must be able to withstand crushing by the greenware located directly above it in the upper regions of the car. The cars may be made to pass through a large kiln where the pellets are sintered thereby producing ceramic carriers that are both rigid and potentially frangible if sufficient force is exerted on the carrier. The carriers may then be physically removed from the cars and stored in large containers, such as steel drums, for storage and subsequent shipment by truck which may subject the carriers to frequent impacts during transit. A carrier's resistance to abrasion may be measured using ASTM D4058-96.

A carrier's surface area and water absorption are two micro physical characteristics commonly used to characterize a carrier. The carrier's surface area is an indication of the amount of surface area per gram of carrier available for the deposition of the catalytically active material. The surface area may be determined using the procedure described by BET (Brunauer, Emmett and Teller) method as described in Journal of the American Chemical Society 60 (1938) pp. 309-316. The carrier's water absorption may be an indication of the carrier's ability to absorb fluids such as the fluids used in the catalyst preparation process to deposit catalytically active metal, promoters and co-promoters onto the carrier's available surface area. Water absorption may be measured using the following procedure. First, approximately 100 g of representative samples of carrier are dried at 110° C. for one hour. The samples are then cooled in a desiccator and the dry mass (D) of each sample is then determined to the nearest 0.01 g. The samples are then placed in a pan of distilled water and boiled for thirty minutes. While the water is boiling, the samples are covered with water and setter pins or some similar device are used to separate the samples from the bottom and sides of the pan and from each other. After the thirty minute boil the samples are allowed to soak for an additional fifteen minutes. After returning to room temperature each sample is then blotted lightly with a moistened, lint-free linen or cotton cloth to remove all excess water from the surface and the saturated mass (M) is determined to the nearest 0.01 g. The blotting operation may be accomplished by rolling the specimen lightly on the wet cloth which shall previously have been saturated with water and then pressed only enough to remove such water as will drip from the cloth. Excessive blotting should be avoided because it will introduce error by withdrawing water from the pores of the sample. The samples should be weighed immediately after blotting. The entire operation should be completed as quickly as possible to minimize errors caused by evaporation of water from the sample. Water absorption (A) is the relationship of the mass of water absorbed to the mass of the dried carrier and is determined using the following formula: $A=[(M-D)/D] \times 100$ wherein the water absorption is expressed as a percent of the weight of the carrier. Water absorption may also be expressed as the weight of the water that can be absorbed into the pores of the carrier relative to the weight of the carrier and therefore reported as grams of water per gram of carrier and the units may be abbreviated as "g/g". Water absorption may also be expressed as cc/g provided there is a correction for the density of water at the conditions measured. A carrier's water absorption value may be positively correlated to and thus used interchangeably with the term "porosity" which, in the field of catalyst carriers, is usually understood to mean the carrier's open cell porosity. As a general rule, there is an inverse correlation between water absorption and crush strength.

Recent trends in ethylene oxide catalyst manufacturing have utilized carriers with increasingly higher surface areas and water absorptions. The latter is typically achieved by incorporation of various pore-forming materials into the carrier mix before firing into formed ceramic bodies, which can impart undesired properties to the finished carrier. One effect of increasing the pore forming agent is the weakening of the formed pellet, which can manifest itself in lower flat plate crush strength or decreased resistance to attrition during handling. Particularly in the case of fixed surface area with increasing water absorption, the resulting catalyst after impregnation with metal containing solution and drying will feature increasingly higher silver surface density. This is a direct result of depositing higher amounts of metal onto a fixed surface area. Without wishing to be bound by theory, it is thought that the increased crowding of metal onto carrier support surfaces promotes the process of sintering of the metal particles, and thus results in loss of catalyst activity. In the current invention, this effect is thought to be mitigated by minimizing the larger pores formed by pore forming agents and accommodating the need for target metal loadings through multiple impregnations of metal containing solution. In this manner, with multiple impregnations on a low water absorption carrier, one can attain metal loadings which are equivalent, based on the mass of metal per unit volume of bulk catalyst, to those obtained with fewer impregnations on a higher water absorption carrier Another micro physical characteristic is the carrier's pore size distribution. The pore size distribution may be measured by a conventional mercury intrusion porosimetry device in which liquid mercury is forced into the pores of a carrier. Greater pressure is needed to force the mercury into the smaller pores and the measurement of pressure increments corresponds to volume increments in the pores penetrated and hence to the size of the pores in the incremental volume. As used herein, the pore size distribution, the median pore diameters and the pore volumes are as measured by mercury intrusion porosimetry to a pressure of $2.1 \times 10^8$ Pa using a Micromeretics Autopore 9200 model (130° contact angle, mercury with a surface tension of 0.480 N/m, and correction for mercury compression applied). As used herein, the median pore diameter is the pore diameter at which half of the total pore volume is contained in pores having a larger pore diameter and half of the total pore volume is contained in pores having a smaller pore diameter.

After the carriers have been manufactured and transported to a catalyst manufacturing facility, they may be exposed to an additional set of physical impacts during the catalyst manufacturing process. For example, after the carriers have been removed from the shipping containers and begin processing through the catalyst manufacturing process they may be exposed to high centrifugal force during a chemical impregnation process which causes individual carriers to collide with other carriers and the interior surface of metal equipment. The force exerted on the catalyst may cause the catalyst to break and/or abrade thereby producing a fine ceramic powder that reduces the quantity of usable catalyst and may clog the catalyst manufacturing equipment. After the catalyst has been manufactured, the catalyst pellets may be dropped into tube shaped reactors that may be between 3 and 25 meters in length and 20 mm to 50 mm in diameter. The thickness of the tube walls may be between 0.5 and 10 mm. If the catalyst pellets break during loading into the reactor the pieces of catalysts could negatively impact the performance of the reactor by increasing the pressure drop, altering the flow of the reactants and byproducts through the reactor, and exposing catalyst surface that does not contain the catalytically active material. Abraded and broken catalyst pellets may cause a reduction in the efficiency of the reactor thereby increasing the cost of the final product.

From a chemical point of view, a carrier's chemical composition may be influenced by several factors including impurities in the raw materials used to make the carriers. An example of a common raw material is alumina, such as alpha alumina, in powder form which is a well-known ingredient for manufacturing catalysts for the production of ethylene oxide and other epoxidation reactions. The impurities in the alpha alumina may depend on the process used to manufacture the alpha alumina. Another class of raw materials known as bond materials typically contain a mixture of elements and compounds that serve to bind the particles of alumina powder into discreet, self-supporting greenware or as a sintered carrier. The phrase "bond material" may include temporary bond material and/or permanent bond material. Temporary bond material, such as polyolefin oxides, celluloses and substituted celluloses, including methylcellulose, starch, ethylcellulose and carboxyethylcellulose, typically enable the greenware to remain intact during the carrier manufacturing process. In contrast to temporary bond materials, permanent bond material usually remains a part of the carrier after it has been sintered. Examples of permanent bond materials include alkaline earth metal compounds and alkali metal compounds.

Preferably, the alkaline earth metal compounds include silicates such as magnesium silicate, calcium silicate and barium silicate. Unfortunately both the temporary bond materials and the permanent bond materials may contain one or more impurities that negatively impact the performance of the catalyst. Another class of raw materials is commonly known as pore formers which are used to induce a desired amount of porosity having a certain pore size distribution. The pore formers are typically removed from the carrier during the sintering of the carrier. The pore formers may be naturally occurring material or manufactured materials. An example of a naturally occurring material is comminuted shells of nuts such as pecan, cashew, walnut, peach, apricot and filbert which may be referred to herein as coarse pore formers. Examples of synthetic materials are polypropylene and/or polyethylene. The quantities and varieties of chemical impurities in the naturally occurring materials are inherently more variable than the quantities and varieties of chemical impurities in the manufactured bond material. Consequently, the residue that remains in a carrier after the naturally occurring pore material has been burned out during sintering may contain a variable number of impurities that can adversely impact the selectivity and longevity of the catalyst. Impurities commonly introduced into the carrier by the pore former include potassium containing compounds. Depending on the combinations and concentrations of the impurities, the impurities may only slightly or, in contrast, significantly impact the performance of the catalyst made therefrom. Other raw materials used to manufacture carriers are fluids such as solvents and extrusion aids. Water, particularly de-ionized water, is the most common solvent. The amount of water used in a particular mix is adjusted to achieve a desired flowability through an extrusion die. Typical quantities of water vary from 10 weight percent to 60 weight percent based on the weight of the alumina. Examples of suitable extrusion aids include petroleum jelly, grease, polyolefin oxides and polyethylene glycol.

Carriers for olefin epoxidation catalysts can be made by different processes that result in carriers having distinct morphologies. In a first process, which is disclosed in U.S. Pat. No. 4,994,589, carrier is made by a process that produces alpha-alumina support particles having a "platelet morphology". FIG. 1 in U.S. Pat. No. 4,994,589 is a scanning electron micrograph of alpha-alumina support particles having a platelet morphology. To produce carrier with the platelet morphology, a "fluorine recrystallizing agent is used in an amount sufficient to effect conversion of the alumina to alpha-alumina having at least one substantially flat surface." "The "substantially flat major surface" referred to herein may be characterized by a radius of curvature of at least about twice the length of the major dimension of the surface. Preferably, the particles also have aspect ratios of at least about 4:1, the aspect ratio being the ratio of the longest or major dimension to the smallest or minor dimension." The process forms alumina having the platelet morphology which, when viewed at high magnification such as 2000×, approximates the shapes of "small plates or wafers". As described in U.S. Pat. No. 4,994,589, "A portion of the support particles preferably are formed as "interfused" or "interpenetrated" platelets, that is, having the appearance of platelets growing out of or passing through one another at various angles." With regard to the quantity of platelet alumina in the carrier, "Preferably, at least about 50 percent of particles of the support having a particle size of at least 0.1 micron comprise particles having at least one substantially flat major surface." Furthermore, "These platelet-type particles frequently have substantially angular edge portions, as contrasted with amorphous or rounded edge portions of conventional support materials, including conventional alpha-alumina supports." In a second process, "conventional" carrier, which may be referred to herein as carrier comprising non-platelet alumina, is made without using a fluorine recrystallizing agent. As described herein, carrier comprising non-platelet alumina, which is also known as non-platelet carrier, has very few, if any, particles of alumina having at least one substantially flat major surface. As used herein, no more than 25 percent of the non-platelet carrier's alumina particles have at least one substantially flat major surface. The second process typically uses small amounts of one or more bond materials to facilitate bonding of the alumina particles to one another. The bond material may partially coat some of the alumina particles and/or may appear to accumulate between the particles thereby forming bond posts. The morphology of the carrier made by the second process impacts physical characteristics of the carrier, such as surface area, water absorption, pore size distribution and particle size.

Inventors of the invention claimed herein have developed and characterized carriers that enable the production of high selectivity catalyst which are also sufficiently robust to withstand the rigors to which a commercially available carrier is exposed during its functional lifetime. Carriers of the present invention are devised to incorporate therein a minimum amount of silica, measured as $SiO_2$, and less than a maximum amount of $Na_2O$. The carriers also have less than a maximum amount of water absorption and the carrier's ratio of water absorption to surface area does not exceed a specified maximum. Carriers having the unique combination of chemical and physical attributes and a process that can be used to make the carriers will now be described.

In one embodiment, a carrier of the present invention has at least 85 weight percent alumina, at least 0.06 weight percent silica measured as $SiO_2$, and no more than 0.04 weight percent $Na_2O$. The percentage of alumina, based on the total weight of the carrier, may be 90 weight percent, 95 weight percent or higher. The quantities of $SiO_2$ and $Na_2O$ are determined using Inductively Coupled Plasma-Optical Emission Spectroscopy (ICP-OES) analysis, wherein the samples are prepared using a fusion process, and are based on the total weight of the carrier after the carrier has been sintered and before the start of any subsequent processing steps that could alter the chemical composition of the carrier. As used herein, the phrase "subsequent processing steps" includes, for example, processes such as wash coating, rinsing, immersion in a liquid, or deposition of an element or compound on the surface of the carrier. The amount of silica in the carrier could be between 0.06 to 0.40 weight percent, such as, 0.08, 0.15, 0.18, 0.20, 0.30 or 0.35 weight percent. Similarly, the amount of $Na_2O$ could be between 0.01 and 0.04 weight percent, such as 0.02 or 0.03 weight percent Unlike some carriers in the prior art that may meet one of the limitations described above, the combination of a minimum amount of silica and no more than a maximum amount of $Na_2O$ is believed to contribute to the creation of a high selectivity catalyst.

With regard to physical characteristics, in one embodiment a carrier of this invention may have a water absorption value no greater than 0.35 gram of water/gram of carrier which may be abbreviated as 0.35 g/g, and a ratio of water absorption to surface area no greater than 0.50 gram of water/$m^2$ of carrier which may be abbreviated as 0.50 g/$m^2$. In some embodiments, a carrier of this invention may have a water absorption less than 0.35 g/g, such as 0.32 or even 0.30 g/g and the ratio of water absorption to surface area may be no greater than 0.45 or 0.40 g/$m^2$. The ratio of water absorption to surface area is determined by measuring the carrier's water absorption as grams of water per gram of carrier and then dividing the water absorption by the carrier's surface area which is measured as $m^2/g$. The combined use of: (1) water absorption; and (2) the ratio of water absorption to surface area inherently limits the surface area of a carrier that has a 0.35 g/g water absorption value to no less than 0.70 $m^2/g$. In some embodiments, the carrier's surface area could be 0.75, 0.80, 0.85 $m^2/g$ and higher. Intermediate surface areas such as 0.78, 0.82 and 0.90 $m^2/g$ are feasible and contemplated. The combined use of water absorption and the ratio of water absorption to surface area also provides for carriers that have a water absorption less than 0.35 g/g to have a surface area less than 0.70 $m^2/g$. For example, if a carrier has a water absorption value of 0.25 g/g then the surface area could be 0.50 $m^2/g$ and the carrier would have a ratio of water absorption to surface area of 0.50 $g/m^2$. In contrast to the low pore volume and low surface area carriers disclosed by Hayden and the high pore volume and high surface area carriers disclosed by Thorsteinson, carriers of this invention may be generally described as low pore volume and high surface area carriers.

In some embodiments, the pore size distribution of a carrier of this invention may have a majority of the carrier's total pore volume contributed by pores having diameters within a narrow range. For example, at least 60 percent of the total pore volume could be contributed by pores within a range of 3.8 microns. In some embodiments, at least 80 percent, 90 percent or more of the total pore volume could be contributed by pores within a range of 3.8 microns. Furthermore, no more than 10, 15 or even 20 percent of the total pore volume may be contributed by pores having a diameter greater than 10 microns. Controlling the pore size distribution of carriers of this invention to distributions wherein the majority of the total pore volume is contributed by pores within a narrow range and limiting the amount of pore volume contributed by large pores (i.e. greater than 10 microns) may help to achieve the desired low pore volume and high surface area characteristics.

The catalyst pellets may have a number of different shapes, with the most common shape being a small cylinder pellet shape with a hole in the center of the pellet. Other possible shapes are disclosed in WO 2004/014549; U.S. Pat. No. 2,408,164 and EP 1,184,077 A1. Preferably, the catalyst particles have a generally hollow cylinder geometric configuration having a length of from 4 to 20 mm, an outside diameter of from 4 to 20 mm, an inside diameter of from 0.1 to 6 mm and a ratio of the length to the outside diameter in the range of from 0.5 to 2.

Preparation of Silver Catalysts

The preparation of the silver catalyst is known in the art and the known methods are applicable to the preparation of the catalyst which may be used in the practice of this invention. Methods of depositing silver on the carrier include impregnating the carrier or carrier bodies with a silver compound containing cationic silver and/or complexed silver and performing a reduction to form metallic silver particles. For further description of such methods, reference may be made to U.S. Pat. No. 5,380,697; U.S. Pat. No. 5,739,075; U.S. Pat. No. 4,766,105 and U.S. Pat. No. 6,368,998, which are incorporated herein by reference. Suitably, silver dispersions, for example silver sols, may be used to deposit silver on the carrier.

The reduction of cationic silver to metallic silver may be accomplished during a step in which the catalyst is dried, so that the reduction as such does not require a separate process step. This may be the case if the silver containing impregnation solution comprises a reducing agent, for example, an oxalate, a lactate or formaldehyde.

When catalysts of different silver contents are prepared on support materials of similar packing densities it is convenient to compare them on a silver weight basis, which is typically expressed in weight percent silver as a function of the total weight of catalyst.

Appreciable catalytic activity is obtained by employing a silver content of the catalyst of at least 1 wt %, relative to the weight of the catalyst. Preferably, the catalyst comprises silver in a quantity of from 5.0 to 50.0 wt %, more preferably from 7.5 to 45.0 wt %, for example 10.5 wt %, or 12.0 wt %, or 19.0 wt %, or 25.0 wt %, or 35.0 wt %. As used herein, unless otherwise specified, the weight of the catalyst is deemed to be the total weight of the catalyst including the weight of the carrier and catalytic components, for example silver, rhenium promoter, first and second co-promoters and further elements, if any.

Alternatively, the silver loading can be expressed in terms of mass of silver per unit volume of catalyst as it is loaded into the reactor tubes. In this way, comparisons of silver loadings between catalysts prepared on support materials of very different bulk packing densities can be made. Ultimately catalyst is loaded into reactor tubes in a defined volume, so this method of comparing silver loadings is most appropriate. Preferably, silver content expressed in this manner are at least 50 $kg/m^3$, relative to the volume of a packed bed of the catalyst. Preferably, the catalyst comprises silver in a quantity of from 50 to 500 $kg/m^3$, more preferably from 100 to 450 $kg/m^3$, for example 140 $kg/m^3$, or 220 $kg/m^3$, or 230 $kg/m^3$, or 250 $kg/m^3$, or 300 $kg/m^3$. As used herein, unless otherwise specified, the weight of silver is deemed to be the weight of silver contained in one cubic meter of the catalyst loaded as rings having an 8 mm (nominal) outside diameter into tubes having a 39 mm inside diameter.

The catalyst for use in this invention additionally comprises a rhenium promoter component deposited on the carrier in a quantity of greater than 1 mmole/kg, relative to the weight of the catalyst. Preferably, the rhenium promoter may be present in a quantity of at least 0.5 mmole/kg, more preferably at least 1.5 mmole/kg, most preferably at least 2 mmole/kg of the catalyst. Preferably, the rhenium promoter may be present in a quantity of at most 500 mmole/kg, more preferably at most 50 mmole/kg, most preferably at most 10 mmole/kg, relative to the weight of the catalyst. Preferably, the rhenium promoter may be present in a quantity in the range of from 1.25 to 50 mmole/kg, more preferably from 1.75 to 25 mmole/kg, most preferably from 2 to 10 mmole/kg, relative to the weight of the catalyst. The form in which the rhenium promoter may be deposited onto the carrier is not material to the invention. For example, the rhenium promoter may suitably be provided as an oxide or as an oxyanion, for example, as a rhenate or perrhenate, in salt or acid form.

The catalyst for use in this invention optionally comprises a first co-promoter component. The first co-promoter may be selected from sulfur, phosphorus, boron, and mixtures thereof. It is particularly preferred that the first co-promoter comprises, as an element, sulfur.

The catalyst for use in this invention may additionally comprise a second co-promoter component. The second co-promoter component may be selected from tungsten, molybdenum, chromium, and mixtures thereof. It is particularly preferred that the second co-promoter component comprises, as an element, tungsten and/or molybdenum, in particular tungsten. The form in which first co-promoter and second co-promoter components may be deposited onto the carrier is not material to the invention. For example, the first co-promoter and second co-promoter components may suitably be provided as an oxide or as an oxyanion, for example, as a tungstate, molybdate, or sulfate, in salt or acid form.

The total quantity of the first co-promoter and the second co-promoter deposited on the carrier is at most 10.0 mmole/kg, calculated as the total quantity of the elements (i.e., the total of sulfur, phosphorous, boron, tungsten, molybdenum and/or chromium) relative to the weight of the catalyst. Preferably, the total quantity of the first co-promoter and the second co-promoter may be at most 4.0 mmole/kg, more preferably at most 3 mmole/kg of catalyst. Preferably, the total quantity of the first co-promoter and the second co-promoter may be at least 0.1 mmole/kg, more preferably at least 0.5 mmole/kg, most preferably at least 1 mmole/kg of the catalyst.

In an embodiment, the molar ratio of the first co-promoter to the second co-promoter may be greater than 1. In this embodiment, the molar ratio of the first co-promoter to the second co-promoter may preferably be at least 1.25, more preferably at least 1.5, most preferably at least 2, in particular at least 2.5. The molar ratio of the first co-promoter to the second co-promoter may be at most 20, preferably at most 15, more preferably at most 10.

In an embodiment, the molar ratio of the rhenium promoter to the second co-promoter may be greater than 1. In this embodiment, the molar ratio of the rhenium promoter to the second co-promoter may preferably be at least 1.25, more preferably at least 1.5. The molar ratio of the rhenium promoter to the second co-promoter may be at most 20, preferably at most 15, more preferably at most 10.

The catalyst may preferably also comprise a further element deposited on the carrier. Eligible further elements may be selected from nitrogen, fluorine, alkali metals, alkaline earth metals, titanium, hafnium, zirconium, vanadium, thallium, thorium, tantalum, niobium, gallium, germanium, and mixtures thereof. Preferably, the alkali metals are selected from lithium, potassium, rubidium and cesium. Most preferably, the alkali metal is lithium, potassium and/or cesium. Preferably, the alkaline earth metals are selected from calcium, magnesium and barium. Preferably, the further element may be present in the catalyst in a total quantity of from 0.01 to 500 mmole/kg, more preferably from 0.05 to 100 mmole/kg, the total quantity of the element relative to the weight of the catalyst. The further element may be provided in any form. For example, salts or hydroxides of an alkali metal or an alkaline earth metal are suitable. For example, lithium compounds may be lithium hydroxide or lithium nitrate.

In an embodiment, the catalyst may preferably further comprise a potassium promoter deposited on the carrier. The additional potassium promoter is preferred especially when the carrier utilized in making the catalyst contains low levels of leachable potassium. For example, the additional potassium promoter is especially preferred when the carrier contains nitric acid leachable potassium in a quantity of less than 85 ppmw, relative to the weight of the carrier, suitably at most 80 ppmw, more suitably at most 75 ppmw, most suitably at most 65 ppmw, same basis. The additional potassium promoter is especially preferred when the carrier contains water leachable potassium in a quantity of less than 40 ppmw, relative to the weight of the carrier, suitably at most 35 ppmw, more suitably at most 30 ppmw. In this embodiment, the potassium promoter may be deposited in a quantity of at least 0.5 mmole/kg, preferably at least 1 mmole/kg, more preferably at least 1.5 mmole/kg, most preferably at least 1.75 mmole/kg, calculated as the total quantity of the potassium deposited relative to the weight of the catalyst. The potassium promoter may be deposited in a quantity of at most 20 mmole/kg, preferably at most 15 mmole/kg, more preferably at most 10 mmole/kg, most preferably at most 5 mmole/kg, on the same basis. The potassium promoter may be deposited in a quantity in the range of from 0.5 to 20 mmole/kg, preferably from 1 to 15 mmole/kg, more preferably from 1.5 to 7.5 mmole/kg, most preferably from 1.75 to 5 mmole/kg, on the same basis. A catalyst prepared in accordance with this embodiment can exhibit an improvement in selectivity, activity, and/or stability of the catalyst especially when operated under conditions where the reaction feed contains low levels of carbon dioxide, described hereinafter.

In an embodiment, the catalyst may preferably contain a quantity of potassium such that the amount of water extractable potassium of the catalyst may be at least 1.25 mmole/kg, relative to the weight of the catalyst, suitably at least 1.5 mmole/kg, more suitably at least 1.75 mmole/kg, same basis. Suitably, the catalyst may contain water extractable potassium in a quantity of at most 10 mmole/kg, more suitably at most 7.5 mmole/kg, most suitably at most 5 mmole/kg, same basis. Suitably, the catalyst may contain water extractable potassium in a quantity in the range of from 1.25 to 10 mmole/kg, more suitably from 1.5 to 7.5 mmole/kg, most suitably from 1.75 to 5 mmole/kg, same basis. The source of water extractable potassium may originate from the carrier and/or the catalytic components. It is important to select a target value for potassium for the entire catalyst composition (carrier plus added catalyst components). For example if the target water extractable quantity of potassium is 10 mmole/g, relative to the weight of the catalyst, such target potassium level is achieved by measuring the potassium level of the carrier and adding sufficient additional potassium during the catalyst impregnation to achieve the target potassium level. A similar process for adding sodium could be applied in order to achieve the proper target level.

The quantity of water extractable potassium in the catalyst is deemed to be the quantity insofar as it can be extracted from the catalyst. The extraction involves extracting a 2-gram sample of the catalyst three times by heating it in 25-gram portions of de-ionized water for 5 minutes at 100° C. and determining in the combined extracts the amount of potassium by using a known method, for example atomic absorption spectroscopy.

As used herein, unless otherwise specified, the quantity of alkali metal present in the catalyst and the quantity of water leachable components present in the carrier are deemed to be the quantity insofar as it can be extracted from the catalyst or carrier with de-ionized water at 100° C. The extraction method involves extracting a 10-gram sample of the catalyst or carrier three times by heating it in 20 ml portions of de-ionized water for 5 minutes at 100° C. and determining in the combined extracts the relevant metals by using a known method, for example atomic absorption spectroscopy.

As used herein, unless otherwise specified, the quantity of alkaline earth metal present in the catalyst and the quantity of acid leachable components present in the carrier are deemed to be the quantity insofar as it can be extracted from the catalyst or carrier with 10% w nitric acid in de-ionized water at 100° C. The extraction method involves extracting a 10-gram sample of the catalyst or carrier by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Epoxidation Process

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process.

The olefin for use in the present epoxidation process may be any olefin, such as an aromatic olefin, for example styrene, or a di-olefin, whether conjugated or not, for example 1,9-decadiene or 1,3-butadiene. Typically, the olefin is a mono-olefin, for example 2-butene or isobutene. Preferably, the olefin is a mono-α-olefin, for example 1-butene or propylene. The most preferred olefin is ethylene. Suitably, mixtures of olefins may be used.

The quantity of olefin present in the feed may be selected within a wide range. Typically, the quantity of olefin present in the feed will be at most 80 mole-%, relative to the total feed. Preferably, it will be in the range of from 0.5 to 70 mole-%, in particular from 1 to 60 mole-%, on the same basis. As used herein, the feed is considered to be the composition which is contacted with the catalyst.

The present epoxidation process may be air-based or oxygen-based, see "Kirk-Othmer Encyclopedia of Chemical Technology", $3^{rd}$ edition, Volume 9, 1980, pp. 445-447. In the air-based process, air or air enriched with oxygen is employed as the source of the oxidizing agent while in the oxygen-based processes high-purity (at least 95 mole-%) or very high purity (at least 99.5 mole-%) oxygen is employed as the source of the oxidizing agent. Reference may be made to U.S. Pat. No. 6,040,467, incorporated by reference, for further description of oxygen-based processes.

The quantity of oxygen present in the feed may be selected within a wide range. However, in practice, oxygen is generally applied in a quantity which avoids the flammable regime. Typically, the quantity of oxygen applied will be within the range of from 1 to 15 mole-%, more typically from 2 to 12 mole-% of the total feed. In order to remain outside the flammable regime, the quantity of oxygen present in the feed may be lowered as the quantity of the olefin is increased. The actual safe operating ranges depend, along with the feed composition, also on the reaction conditions such as the reaction temperature and the pressure.

A reaction modifier may be present in the feed for increasing the selectively, suppressing the undesirable oxidation of olefin or olefin oxide to carbon dioxide and water, relative to the desired formation of olefin oxide. Many organic compounds, especially organic halides and organic nitrogen compounds, may be employed as the reaction modifiers. Nitrogen oxides, organic nitro compounds such as nitromethane, nitroethane, and nitropropane, hydrazine, hydroxylamine or ammonia may be employed as well. It is frequently considered that under the operating conditions of olefin epoxidation the nitrogen-containing reaction modifiers are precursors of nitrates or nitrites, i.e. they are so-called nitrate- or nitrite-forming compounds. Reference may be made to EP-A-3642 and U.S. Pat. No. 4,822,900, which are incorporated herein by reference, for further description of nitrogen-containing reaction modifiers.

Organic halides are the preferred reaction modifiers, in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride, vinyl chloride and ethylene dichloride. Additional disclosure regarding reaction modifiers can be found in, for example, U.S. Pat. No. 7,193,094.

Suitable nitrogen oxides are of the general formula $NO_x$ wherein x is in the range of from 1 to 2, and include for example NO, $N_2O_3$ and $N_2O_4$. Suitable organic nitrogen compounds are nitro compounds, nitroso compounds, amines, nitrates and nitrites, for example nitromethane, 1-nitropropane or 2-nitropropane. In preferred embodiments, nitrate- or nitrite-forming compounds, e.g. nitrogen oxides and/or organic nitrogen compounds, are used together with an organic halide, in particular an organic chloride.

The reaction modifiers are generally effective when used in small quantities in the feed, for example up to 0.1 mole-%, relative to the total feed, for example from $0.01 \times 10^{-4}$ to 0.01 mole-%. In particular when the olefin is ethylene, it is preferred that the reaction modifier is present in the feed in a quantity of from $0.1 \times 10^{-4}$ to $500 \times 10^{-4}$ mole-%, in particular from $0.2 \times 10^{-4}$ to $200 \times 10^{-4}$ mole-%, relative to the total feed.

In addition to the olefin, oxygen and the reaction modifier, the feed may contain one or more optional components, such as carbon dioxide, inert gases and saturated hydrocarbons. Carbon dioxide is a by-product in the epoxidation process. However, carbon dioxide generally has an adverse effect on the catalyst activity. Typically, a quantity of carbon dioxide in the feed in excess of 25 mole-%, preferably in excess of 10 mole-%, relative to the total feed, is avoided. A quantity of carbon dioxide of less than 6 mole-%, preferably less than 3 mole-%, in particular in the range of from 0.3 to less than 1 mole-%, relative to the total feed, may be employed. Under commercial operations, a quantity of carbon dioxide of at least 0.1 mole-%, or at least 0.2 mole-%, relative to the total feed, may be present in the feed. Inert gases, for example nitrogen or argon, may be present in the feed in a quantity of from 30 to 90 mole-%, typically from 40 to 80 mole-%. Suitable saturated hydrocarbons are methane and ethane. If saturated hydrocarbons are present, they may be present in a quantity of up to 80 mole-%, relative to the total feed, in particular up to 75 mole-%. Frequently, they are present in a quantity of at least 30 mole-%, more frequently at least 40 mole-%. Saturated hydrocarbons may be added to the feed in order to increase the oxygen flammability limit.

The epoxidation process may be carried out using reaction temperatures selected from a wide range. Preferably the reaction temperature is in the range of from 150 to 325° C., more preferably in the range of from 180 to 300° C.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is a gas phase process involving a packed catalyst bed, the GHSV is in the range of from 1,500 to 10,000 $h^{-1}$. Preferably, the process is carried out at a work rate in the range of from 0.5 to 10 kmole olefin oxide produced per $m^3$ of catalyst per hour, in particular 0.7 to 8 kmole olefin oxide produced per $m^3$ of catalyst per hour, for example 5 kmole olefin oxide produced per $m^3$ of catalyst per hour. As used herein, the work rate is the amount of the olefin oxide produced per unit volume of catalyst per hour and the selectivity is the molar quantity of the olefin oxide formed relative to the molar quantity of the olefin converted. Suitably, the process is conducted under conditions where the olefin oxide partial pressure in the product mix is in the range of from 5 to 200 kPa, for example 11 kPa, 27 kPa, 56 kPa, 77 kPa, 136 kPa, and 160 kPa. The term "product mix" as used herein is understood to refer to the product recovered from the outlet of an epoxidation reactor.

The olefin oxide produced may be recovered from the product mix by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol, a 1,2-diol ether, a 1,2-carbonate, or an alkanolamine.

Conversion of Olefin Oxide to Other Chemicals

The olefin oxide produced in the epoxidation process may be converted into a 1,2-diol, a 1,2-diol ether, a 1,2-carbonate, or an alkanolamine. As this invention leads to a more attractive process for the production of the olefin oxide, it concurrently leads to a more attractive process which comprises producing the olefin oxide in accordance with the invention and the subsequent use of the obtained olefin oxide in the manufacture of the 1,2-diol, 1,2-diol ether, 1,2-carbonate, and/or alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a tenfold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. The presence of such a large quantity of water may favor the selective formation of 1,2-diol and may function as a sink for the reaction exotherm, helping control the reaction temperature. If the proportion of water is lowered, the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

The conversion into the alkanolamine may comprise, for example, reacting the olefin oxide with ammonia. Anhydrous ammonia is typically used to favor the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The 1,2-carbonates may be used as a diluent, in particular as a solvent Alkanolamines may be used, for example, in the treating ("sweetening") of natural gas.

Unless specified otherwise, the low-molecular weight organic compounds mentioned herein, for example the olefins, 1,2-diols, 1,2-diol ethers, 1,2-carbonates, alkanolamines, and reaction modifiers, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Illustrative Embodiments

Preparation of Carrier Samples

Processes for manufacturing carriers for use in epoxidation reactions are described in numerous publications including U.S. Pat. No. 5,100,859 and U.S. Pat. No. 6,831,037 which are incorporated herein by reference. See, for example, the disclosure in U.S. Pat. No. 5,100,859 which begins at column 2, line 6 and continues to column 6, line 43.

Carrier A

First Comparative Example

Carrier A was prepared according to the teachings in U.S. Pat. No. 5,100,859 that pertain to Carrier L. The alumina powder was combined with zirconia, magnesium silicate, walnut shell flour, boric acid and extrusion aid to create a mixture which was then extruded to form hollow cylinders that were dried and fired. The physical and chemical characteristics of the fired cylinders, which may be referred to as carriers or supports, were determined using standard analytical techniques and the data is shown below in Table I. Carrier A's water absorption was 0.489 g/g, the ratio of water absorption to surface area was 0.64 g/m$^2$ and the attrition was 16.8%.

Carrier B

Carrier of this Invention

Carrier B was made by following the disclosure in U.S. Pat. No. 5,100,859 as it pertains to the process for manufacturing Carrier L, shown in Table 5, except for the use of burn-out, which was excluded. The incorporation of a coarse pore former, such as ground shells, may be avoided or limited to less than 0.01 weight percent based on the weight of the alumina. Preferably, the use of a pore former is avoided. The alpha alumina used in the carrier preparation had a purity greater than 98.5 weight percent and the level of certain impurities were controlled to insure that the carrier had the desired chemical composition. Using an alumina powder that had a low amount of sodium led to a carrier wherein the amount of soda in the carrier was no more than 0.04 weight percent. The alumina powder was mixed with magnesium silicate, which functioned as a permanent bond, and contributed to elevating the total quantity of silica in the carrier to at least 0.06 weight percent based on the weight of the alumina. Unlike carrier L in U.S. Pat. No. 5,100,859, Carrier B did not include walnut shell flour which may be referred to as a coarse pore former. The lack of a pore former in Carrier B's formulation is believed to be the reason why Carrier B had a monomodal pore size distribution compared to Carrier A which included a pore former and had a bimodal pore size distribution. The physical and chemical characteristics of Carrier B are shown below in Table 1. Carrier B's water absorption was 0.271 g/g, the ratio of water absorption to surface area was 0.36 g/m$^2$ and the attrition was 6.9%. The $Na_2O$ content was 0.02 weight percent and the silica content was 0.24 weight percent.

Carrier C

Second Comparative Example

Carrier C was a commercially available carrier provided by Saint-Gobain NorPro of Stow, Ohio USA. This carrier's commercial designation is SA 5202. The physical and chemical characteristics of an SA 5502 carrier are disclosed in U.S. Pat. No. 5,187,140 at column 43. The numerical designation 5202 indicates that the shape of the carrier is a sphere while 5502 indicates that the shape of the carrier is a hollow cylinder. The numbers "02" are indicative of the formula used to make the carrier and thereby indicates that the 5202 spheres and 5502 cylinders were made using the same formula. The physical and chemical characteristics of Carrier C, which are recorded in Table 1, reveal a water absorption of 0.247 g/g, a ratio of water absorption to surface area of 0.29 g/m², a soda content of 0.10 percent by weight of the carrier and a silica content of 0.03 percent by weight of the carrier.

TABLE 1

Carrier Properties

| | A comparative | B invention | C comparative |
|---|---|---|---|
| Chemical Analysis[a] | | | |
| Na$_2$O | 0.03 | 0.02 | 0.10 |
| SiO$_2$ | 0.26 | 0.24 | 0.03 |
| Pore Size Distribution | Bi-modal | Mono-modal | Mono-modal |
| Physical Properties | | | |
| Water Absorption (gram of water/gram of carrier) | 0.489 | 0.271 | 0.247 |
| Surface Area (m²/g) | 0.76 | 0.76 | 0.84 |
| Ratio of Water Absorption to Surface Area (g/m²) | 0.64 | 0.36 | 0.29 |
| Bulk Packing Density kg/m³ (lbs/ft³) | 698 (43.6) | 992 (61.9) | 1148 (71.7) |
| Attrition Loss, % | 16.8 | 6.9 | NA[b] |
| Average Flat Plate Crush Strength, N (lbf) | 86.7 (19.5) | 116 (26.0) | NA[b] |

[a] % wt of the carrier
[b] data not available for comparison because Carrier C was shaped as a sphere and Carriers A and B were hollow cylinders.

Analysis of the data in Table 1 reveals the following distinctions between carriers A, B and C. In contrast to Carrier C which has a silica content of 0.03 weight percent and a soda content of 0.10 weight percent, Carrier B, which is a carrier of this invention, has a silica content of 0.24 weight percent and a soda content of 0.02 weight percent. Clearly, the silica content of Carrier B is well above the silica content of Carrier C and the soda content of Carrier B is well below the soda content of Carrier C. In contrast to Carrier A which has a bimodal pore size distribution, a water absorption of 0.489 g/g and a ratio of water absorption to surface area of 0.64 g/m², Carrier B has monomodal pore size distribution, a water absorption of 0.271 g/g and a ratio of water absorption to surface area of 0.36 g/m². Carrier B's unique combination of: (1) low water absorption, defined herein as less than 0.35 g/g; (2) high surface area, defined herein as greater than 0.70 m²/g; (3) a silica content between 0.06 and 0.40% by weight of the carrier; and (4) low soda content, defined herein as less than 0.04 weight percent, are believed to contribute to the performance of catalysts made from Carrier B as demonstrated by the selectivity data in Table 4 which is shown below in the Catalysts Examples portion of this specification.

Figure 1B:
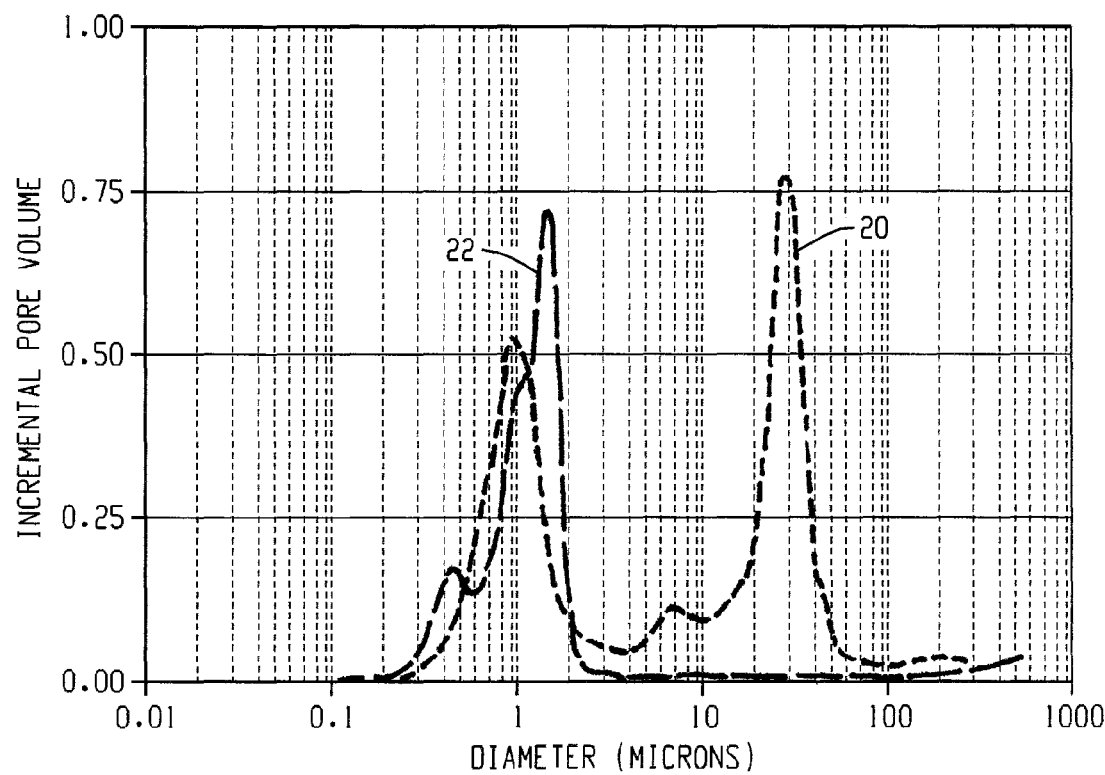
Figure 2A:
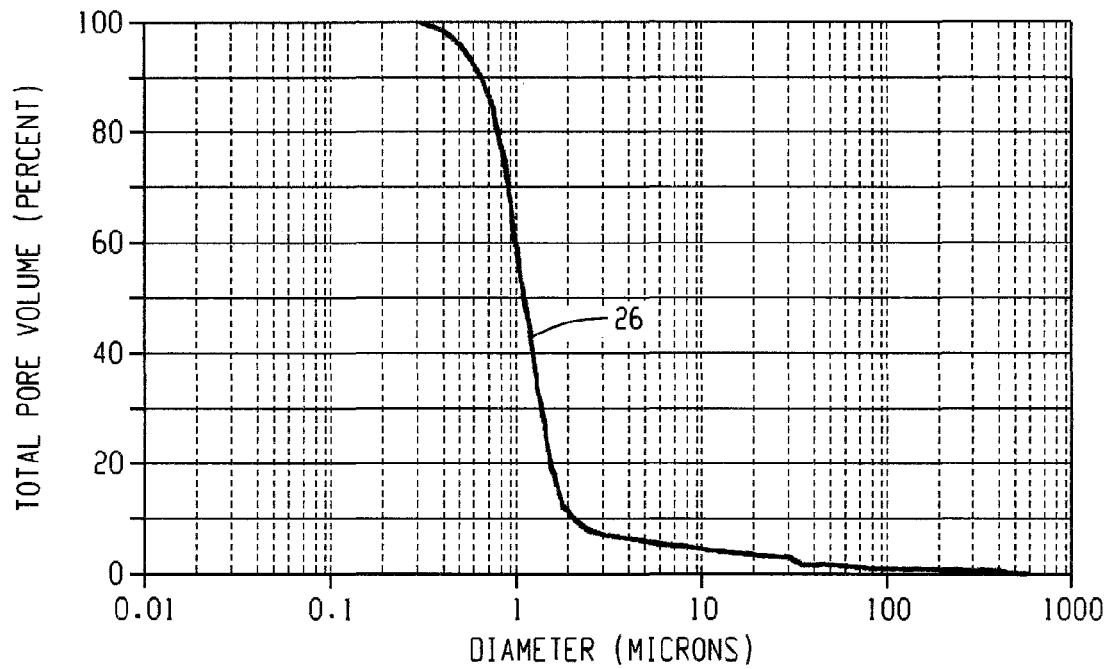
FIG. 2 A is a graph of total pore volume curves.
Figure 2B:
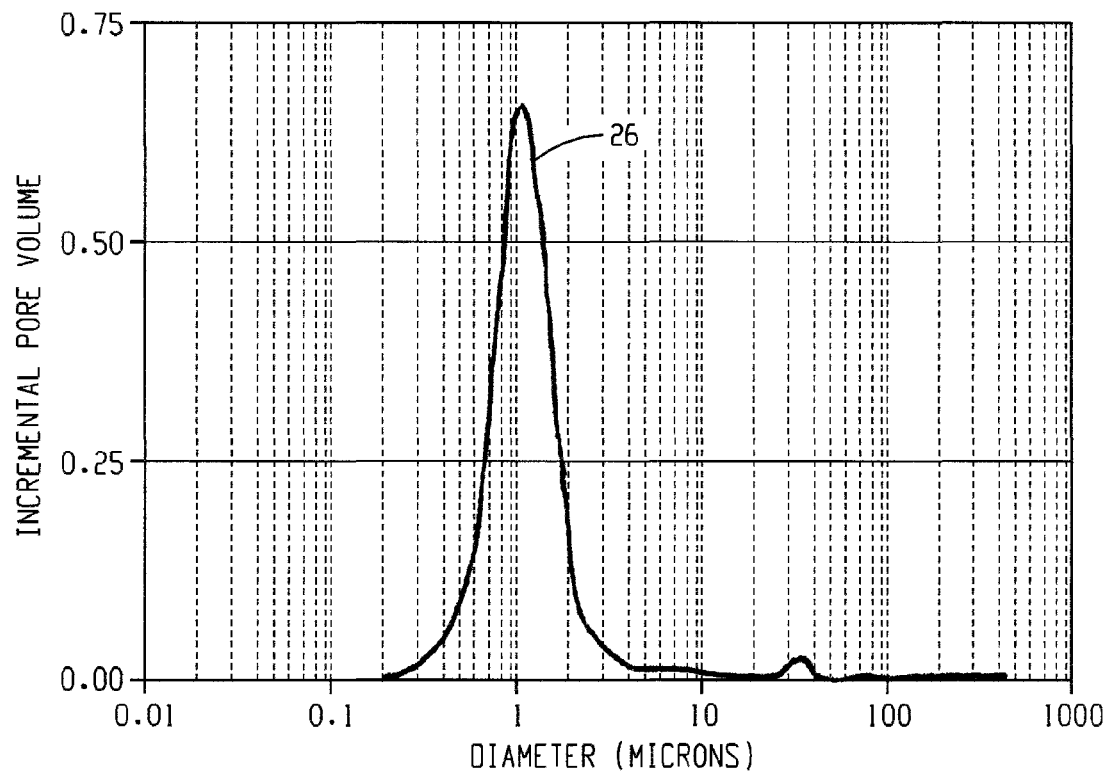

Shown in FIGS. 1A and 1B are the Total Pore Volume curves and the Incremental Pore Volume curves, respectively, for carriers A and C wherein line 20 represents carrier A and line 22 represents carrier C. Shown in FIGS. 2A and 2B are the Total Pore Volume curve and the Incremental Pore Volume curve, respectively, for carrier B which is identified as line 26.

Shown below in Table 2 are the percentages of total pore volume with a specified range of pore diameters. The data clearly illustrates that carrier A has a bimodal pore size distribution with only 42% of the total pore volume contributed by pores having a net range of less than 3.8 microns. In contrast, carriers B and C have 95% and 94%, respectively, of their total pore volumes contributed by pores within a net range of 3.8 microns. Furthermore, the monomodal nature of carrier B pore size distribution is visually discernable in FIG. 2A and objectively quantified in Table 2 wherein 83% of carrier B's total pore volume is contributed by pores with a net range of 1.4 microns. In contrast, only 33% of carrier A's total pore volume is contributed by pores within a net range of 1.4 microns.

TABLE 2

| Net Range of Pore Diameters | Lower Pore Diameter Limit | Upper Pore Diameter Limit | Carrier Designation | | |
|---|---|---|---|---|---|
| | | | A[1] | B[1] | C[1] |
| 3.8 | 0.2 | 4.0 | 42 | 95 | 94 |
| 2.6 | 0.4 | 3.0 | 39 | 92 | 87 |
| 1.4 | 0.6 | 2.0 | 33 | 83 | 76 |

[1] Percentage of total pore volume within specified range.

Preparation of Catalyst Examples

Preparation of Stock Silver Solution

Standard silver solutions were used in all catalyst preparations. A typical solution composition range of major components before dilution is 25-35 wt % Ag⁺, 15-20 wt % ethylene diamine, 10-14 wt % $C_2O_4^{-2}$ and 40-50 wt % $H_2O$. In each of the following catalyst preparation examples, dopants and diluents were added to this stock solution to give the final impregnating solution. The amount of diluent added to the stock solution was based upon the stock solution specific gravity, the carrier water absorption, and the target silver loading for the final catalyst.

Preparation of Catalysts

The three carriers A, B and C described above were used in preparing catalysts according to Examples 1-7.

Example 1 (Comparative)

Preparation of Catalyst Based on Carrier A

Catalyst 1 was prepared by the following procedure: To 192.2 grams of stock silver solution of specific gravity 1.549 g/ml was added 0.1793 g of ammonium perrhenate in 2 g of 1:1 ethylenediamine/water; 0.0500 g of ammonium metatungstate dissolved in 2 g of 1:1 ammonia/water; 0.0855 g of ammonium sulfate dissolved in 2 g of water; 0.2664 g of lithium hydroxide monohydrate dissolved in water, and 0.0676 g potassium nitrate dissolved in 2 g water. Additional water was added to adjust the specific gravity of the solution to 1.501 g/ml. 50 g of the resulting solution was mixed with 0.1045 g of 50% w cesium hydroxide solution, producing the final impregnation solution. A vessel containing 30 grams of Carrier A hollow cylinders was evacuated to 20 mm Hg for 1 minute and the final impregnation solution was added to the carrier pellets while under vacuum, then the vacuum was released and the carrier allowed to contact the liquid for 3 minutes. The impregnated carrier was then centrifuged at 500 rpm for 2 minutes to remove excess liquid. The wet carrier pellets were placed in a vibrating shaker and dried in air flowing at a rate of 16.2 Nl/h at 250° C. for 5.5 minutes producing Catalyst 1.

The final composition of Catalyst 1 comprised the following, calculated on the basis of pore volume impregnation: 17.5% w silver; 2.0 micromole Re/g; 0.6 micromole W/g; 2.0 micromole S/g; 21 micromole Li/g; 2.0 micromole K/g, and 4.5 micromole Cs/g. These values are relative to the weight of the catalyst.

Example 2 (Inventive)

Preparation of Catalyst Based on Carrier B

Catalyst 2 was prepared in two impregnation steps. Approximately 120 grams of Carrier B was first impregnated with 204 grams of silver solution having a specific gravity of 1.478 g/cc according to the procedure for Catalyst 1, except that no dopants were added to the silver solution. The resulting dried catalyst precursor contained approximately 9.8 wt % silver. The dried Catalyst 2 Precursor was then impregnated with a second solution which was made by mixing 191.0 grams of silver stock solution of specific gravity 1.55 g/cc with a solution of 0.3375 g of $NH_4ReO_4$ in 2 g of 1:1 $EDA/H_2O$, 0.0941 g of ammonium metatungstate dissolved in 2 g of 1:1 ammonia/water, 0.1610 g $Li_2SO_4.H_2O$, 0.1272 g $KNO_3$, and 0.5015 g $LiOH.H_2O$ dissolved in water. Additional water was added to adjust the specific gravity of the solution to 1.478 g/cc. 50 grams of such doped solution was mixed with 0.2109 g of 44.8 wt % CsOH solution. This final impregnation solution was used to prepare Catalyst 2. A flask containing 30 grams of the Catalyst 2 Precursor was evacuated to 20 mm Hg for 1 minute and the final impregnation solution was added while under vacuum, then the vacuum was released and the precursor allowed to contact the liquid for 3 minutes. The impregnated precursor was then centrifuged at 500 rpm for 2 minutes to remove excess liquid. The wet Catalyst 2 pellets were placed in a vibrating shaker and dried in air flowing at a rate of 460 SCFH at 250° C. for 5.5 minutes. The final Catalyst 2 composition was 17.5% Ag, 600 ppm Cs/g catalyst, 2.0 µmole Re/g catalyst, 0.60 µmole W/g catalyst, 2.0 S/g catalyst, 2.0 micromole K/g catalyst, and 21 µmole Li/g catalyst.

Example 3 (Inventive)

Preparation of Catalyst Based on Carrier B

Catalyst 3 was prepared in three impregnation steps. Approximately 120 grams of Carrier B was first impregnated with 204 grams of silver solution having a specific gravity of 1.549 g/cc according to the procedure for catalyst 1, except that no dopants were added to the silver solution. The impregnation/centrifuge/drying procedure was performed a total of two times, resulting in a dried catalyst precursor containing approximately 19.5 wt % silver. The dried Catalyst 3 Precursor was then impregnated with a final solution which was made by mixing 191.9 grams of silver stock solution of specific gravity 1.549 g/cc with a solution of 0.3962 g of $NH_4ReO_4$ in 2 g of 1:1 $EDA/H_2O$, 0.1105 g of ammonium metatungstate dissolved in 2 g of 1:1 ammonia/water, 0.1890 g $Li_2SO_4.H_2O$, 0.1493 g $KNO_3$, and 0.5888 g $LiOH.H_2O$ dissolved in water. Additional water was added to adjust specific gravity of the solution to 1.500 g/cc. To 50 grams of such doped solution was added 0.2160 g of 47.02 wt % CsOH solution. This final impregnation solution was used to prepare Catalyst 3. A flask containing 30 grams of the Catalyst 3 Precursor was evacuated to 20 mm Hg for 1 minute and the final impregnation solution was added while under vacuum, then the vacuum was released and the precursor allowed to contact the liquid for 3 minutes. The impregnated precursor was then centrifuged at 500 rpm for 2 minutes to remove excess liquid. Catalyst 3 pellets were placed in a vibrating shaker and dried in air flowing at a rate of 460 SCFH at 250° C. for 5.5 minutes. The final Catalyst 3 composition was 25.7% Ag, 550 ppm Cs/g catalyst, 2.0 µmole Re/g catalyst, 0.60 µmole W/g catalyst, 2.0 S/g catalyst, 2.0 micromole K/g catalyst, and 21 µmole Li/g catalyst.

Example 4 (Comparative)

Preparation of Catalyst Based on Carrier C

Catalyst 4 was prepared in two impregnation steps. Approximately 250 grams of Carrier C was first impregnated with 370 grams of silver solution having a specific gravity of 1.478 g/cc according to the procedure for Catalyst 1, except that no dopants were added to the silver solution. The resulting dried catalyst precursor contained approximately 9.0 wt % silver. The dried Catalyst 4 Precursor was then impregnated with a second solution which was made by mixing 370.5 grams of silver stock solution of specific gravity 1.554 g/cc with a solution of 0.5112 g of $NH_4ReO_4$ in 2 g of 1:1 $EDA/H_2O$, 0.1420 g of ammonium metatungstate dissolved in 2 g of 1:1 ammonia/water, 0.2095 g $Li_2SO_4.H_2O$, 0.1927 g $KNO_3$, and 0.7561 g $LiOH.H_2O$ dissolved in water. Additional water was added to adjust the specific gravity of the solution to 1.478 g/cc. 50 grams of such doped solution was mixed with 0.2438 g of 47.0 wt % CsOH solution. This final impregnation solution was used to prepare Catalyst 4. A flask containing 30 grams of the Catalyst 4 Precursor was evacuated to 20 mm Hg for 1 minute and the final impregnation solution was added while under vacuum, then the vacuum was released and the precursor allowed to contact the liquid for 3 minutes. The impregnated precursor was then centrifuged at 500 rpm for 2 minutes to remove excess liquid. The wet Catalyst 4 pellets were placed in a vibrating shaker and dried in air flowing at a rate of 460 SCFH at 250° C. for 5.5 minutes. The final Catalyst 4 composition was 16.2% Ag, 675 ppm Cs/g catalyst, 2.75 µmole Re/g catalyst, 0.822 µmole W/g catalyst, 2.75 S/g catalyst, 2.75 micromole K/g catalyst, and 29 µmole Li/g catalyst.

Example 5 (Comparative)

Preparation of Catalyst Based on Carrier C

Catalyst 5 was prepared using the solution prepared according to the procedure in Example 4, except that 0.2167 g of 47.0 wt % CsOH solution was used, resulting in a final cesium content of 600 ppmw.

Example 6 (Comparative)

Preparation of Catalyst Based on Carrier C

Catalyst 6 was prepared using the solution prepared according to the procedure in Example 4, except that 0.1626 g 47.0 wt % CsOH solution was used, resulting in a final cesium content of 450 ppmw.

Example 7 (Comparative)

Preparation of Catalyst Based on Carrier C

Catalyst 7 was prepared using the solution prepared according to the procedure in Example 4, except that the dopant amounts were adjusted so as to give the final Catalyst 7 composition of 16.2% Ag, 600 ppm Cs/g catalyst, 2.0 μmole Re/g catalyst, 0.60 μmole W/g catalyst, 2.0 S/g catalyst, 2.0 micromole K/g catalyst, and 21 μmole Li/g catalyst.

TABLE 3

Compositions of Catalysts described in Examples 1-7. Dopant values reported in micromoles dopant per gram of catalyst.

| Example | Ag loading (wt %) | Re | W | S | Li | K | Cs |
|---|---|---|---|---|---|---|---|
| 1 | 17.0 | 2.0 | 0.6 | 2.0 | 21 | 2.0 | 4.51 |
| 2 [a] | 17.0 | 2.0 | 0.6 | 2.0 | 21 | 2.0 | 4.51 |
| 3 [a] | 25.7 | 2.0 | 0.6 | 2.0 | 21 | 2.0 | 4.14 |
| 4 | 16.2 | 2.75 | 0.82 | 2.75 | 29 | 2.75 | 5.08 |
| 5 | 16.2 | 2.75 | 0.82 | 2.75 | 29 | 2.75 | 4.51 |
| 6 | 16.2 | 2.75 | 0.82 | 2.75 | 29 | 2.75 | 3.39 |
| 7 | 16.2 | 2.0 | 0.6 | 2.0 | 21 | 2.0 | 4.51 |

[a] According to the invention

Catalyst Testing

The catalysts described above were used to produce ethylene oxide from ethylene and oxygen. To do this, 3 to 7 g of the crushed catalyst samples were loaded into separate stainless steel U-shaped tubes. Each tube was immersed in a molten metal bath (heat medium) and the ends were connected to a gas flow system. The weight of catalyst used and the inlet gas flow rate were adjusted to give a gas hourly space velocity of 3300 Nl/(l·h), as calculated for uncrushed catalyst. The inlet gas pressure was 1550 kPa (absolute).

Prior to startup, the catalysts were pre-treated for 3 hours with a gas mixture of 11.4 mole-% oxygen, 7 mole-% carbon dioxide and 81.6 mole-% nitrogen at 280° C. Then the reactor was cooled to 240° C., and testing gas mixture was introduced. The gas mixture passed through the catalyst bed, in a "once-through" operation, during the entire test run including the start-up, consisted of 30.0 volume percent ethylene, 8.0 volume percent oxygen, 5.0 volume percent carbon dioxide, 57 volume percent nitrogen and 0 to 6.0 parts per million by volume (ppmv) ethyl chloride. The temperature then adjusted so as to achieve a constant ethylene oxide content of 3.09 volume percent in the outlet gas stream. The quantity of ethyl chloride was varied to obtain maximum selectivity to ethylene oxide. Initial performance data at this production level was measured between 1 to 7 days of operation. The performance data is summarized below in Table 4. Selectivity and temperature values corresponding to increasing cumulative ethylene oxide production would also be measured in order to obtain catalyst stability data.

TABLE 4

Properties and Performance of Catalysts from Examples 1-7.

| Example | Carrier | Ag loading (wt %) | Ag Loading (kg Ag/m³ bulk catalyst) [a] | Cesium (ppmw) | Cesium (ppmw/m² carrier) | Sel. (%) | Temp. (° C.) |
|---|---|---|---|---|---|---|---|
| 1 | A | 17.0 | 140 | 600 | 789 | 87.5 | 272 |
| 2 [b] | B | 17.0 | 230 | 600 | 789 | 88.5 | 259 |
| 3 [b] | B | 25.7 | 320 | 550 | 724 | 88.8 | 250 |
| 4 | C | 16.2 | 220 | 675 | 804 | 80.1 | 253 |
| 5 | C | 16.2 | 220 | 600 | 714 | 80.7 | 247 |
| 6 | C | 16.2 | 220 | 450 | 536 | 84.7 | 250 |
| 7 | C | 16.2 | 220 | 600 | 714 | 79.8 | 257 |

[a] Based on loading of 8 mm (nominal outside diameter) rings in a 39 mm (inside diameter) packed tube
[b] According to the invention It can be seen from the examples set forth that the inventive carrier can be used to make silver epoxidation catalysts with distinct advantage over prior art carriers. Comparing Examples 1 and 2, wherein the carriers differ in water absorption, it is apparent that of catalysts with equivalent weight basis metal loading, the advantage in both selectivity and activity is with the inventive carrier—that with an equivalent surface area but lower water absorption. A further improvement in activity is found on the inventive carrier with increased metal loading (Examples 2 and 3). Examples 2 and 7 illustrate the remarkable difference between the inventive carrier and the prior art material of similar physical properties. Examples 4, 5, and 6 are added for completeness in order to remove the question of dopant surface density in the case of the slightly higher surface area of carrier C. In these examples, the dopants were increased by the same factor as the surface area difference between Carrier B and Carrier C. Examples 2 and 4 are the best comparison in this series, with very similar cesium content. These data show that when we adjust the dopants to normalize the surface area difference, there is still a clear advantage for the catalyst made on inventive Carrier B. All the data taken together illustrate an advantage for carriers made with low water absorption, and of defined chemical composition.

In addition to the advantages found in initial performance of the inventive examples, certain embodiments of this invention could be useful in providing catalysts with improved stability of selectivity and/or activity. Such improved longevity provides economic benefit for the catalyst user.

The above description is considered that of particular embodiments only. Modifications of the invention will occur to those skilled in the art and to those who make or use the invention. Therefore, it is understood that the embodiments shown in the drawings and described above are merely for illustrative purposes and are not intended to limit the scope of the invention, which is defined by the following claims as interpreted according to the principles of patent law, including the Doctrine of Equivalents.

What is claimed is:

1. A carrier comprising at least 85 wt percent alpha alumina, at least 0.06 wt percent $SiO_2$ and no more than 0.04 wt percent $Na_2O$, said carrier comprising a water absorption no greater than 0.35 gram of water/gram of carrier and a ratio of water absorption (gram of water/gram of carrier) to surface area ($m^2$ of carrier/gram of carrier) no greater than 0.50 gram of water/$m^2$ of carrier.

2. The carrier of claim 1 wherein said $SiO_2$ does not exceed 0.40 wt percent.

3. The carrier of claim 1 wherein said $SiO_2$ does not exceed 0.30 wt percent.

4. The carrier of claim 1 wherein said $Na_2O$ does not exceed 0.03 wt percent.

5. The carrier of claim 1 wherein said carrier comprises at least 0.15 wt percent $SiO_2$.

6. The carrier of claim 1 wherein said ratio does not exceed 0.45 g/m$^2$.

7. The carrier of claim 1 wherein said ratio does not exceed 0.40 g/m$^2$.

8. The carrier of claim 1 wherein said water absorption does not exceed 0.30 g/g.

9. The carrier of claim 8 wherein said surface area exceeds 0.70 m$^2$/g.

10. The carrier of claim 1 wherein said surface area exceeds 0.75 m$^2$/g.

11. The carrier of claim 1, wherein said carrier further comprises a total pore volume and at least 60% of the total pore volume is contributed by pores having diameters within a range no greater than 3.8 microns.

12. The carrier of claim 1 wherein at least 80% of the total pore volume is contributed by pores having diameters within a range no greater than 3.8 microns.

13. The carrier of claim 1, wherein at least 90% of the total pore volume is contributed by pores having diameters within a range no greater than 3.8 microns.

14. The carrier of claim 1 wherein said carrier has a total pore volume and no more than 20% of said total pore volume is contributed by pores greater than 10 microns.

15. The carrier of claim 1 wherein no more than 5 of said total pore volume is contributed by pores greater than 10 microns.

16. The carrier of claim 1 wherein no more than 10% of said total pore volume is contributed by pores greater than 10 microns.

17. The carrier of claim 1 wherein said carrier comprises a bond material.

18. The carrier of claim 1 wherein said carrier comprises non-platelet morphology.

* * * * *